United States Patent [19]

Harvey et al.

[11] Patent Number: 6,001,895
[45] Date of Patent: Dec. 14, 1999

[54] COMPOSITE SURGICAL MATERIAL

[75] Inventors: Wilson Harvey, Sterling; Nicholas D. Light, Doune Perthshire; Carla A. Haynes, Glasgow, all of United Kingdom

[73] Assignee: Johnson & Johnson Medical, Inc., Arlington, Tex.

[21] Appl. No.: 08/994,276

[22] Filed: Dec. 19, 1997

Related U.S. Application Data

[60] Continuation-in-part of application No. 08/437,905, May 10, 1995, Pat. No. 5,660,857, which is a division of application No. 08/035,001, Mar. 22, 1993, abandoned, and a division of application No. 08/280,916, Jul. 27, 1994, Pat. No. 5,789,465.

[30] Foreign Application Priority Data

Jul. 28, 1993 [GB] United Kingdom ............... 9315614
Sep. 17, 1993 [GB] United Kingdom ............... 9319273

[51] Int. Cl.$^6$ ........................................... A61F 2/00
[52] U.S. Cl. .............. 523/113; 523/105; 524/801; 524/21; 424/426; 424/427; 424/489; 427/2.24; 525/450; 528/361
[58] Field of Search ................... 523/105, 113; 525/450; 528/361; 424/427, 426, 489; 427/2.24; 524/21

[56] References Cited

U.S. PATENT DOCUMENTS

| 4,685,883 | 8/1987 | Jernberg . |
| 4,764,377 | 8/1988 | Goodson . |
| 4,789,662 | 12/1988 | Thomas-Leurrquin et al. . |
| 4,849,141 | 7/1989 | Fujioka et al. . |
| 4,892,736 | 1/1990 | Goodson . |
| 4,906,670 | 3/1990 | Higashi et al. . |
| 4,933,182 | 6/1990 | Higashi et al. . |
| 4,961,707 | 10/1990 | Magnusson et al. . |
| 5,002,769 | 3/1991 | Friedman . |
| 5,037,377 | 8/1991 | Alonso . |
| 5,198,220 | 3/1993 | Damani . |
| 5,447,940 | 9/1995 | Harvey et al. ............... 514/310 |
| 5,660,857 | 8/1997 | Haynes et al. ............... 424/450 |

FOREIGN PATENT DOCUMENTS

| 0 194192 | 9/1986 | European Pat. Off. . |
| 0 297535 | 1/1989 | European Pat. Off. . |
| WO 90/13302 | 11/1990 | European Pat. Off. . |
| 0 567234 | 10/1993 | European Pat. Off. . |
| 0 140 766 | 5/1985 | United Kingdom . |
| 0 250187 | 12/1987 | United Kingdom . |

OTHER PUBLICATIONS

European Patent Standard Search Report for EP 94305536.8 dated Nov. 15, 1994.

*Primary Examiner*—Andrew E. C. Merriam
*Attorney, Agent, or Firm*—Andrew C. Farmer; Theodore J. Shatynski

[57] ABSTRACT

A composite surgical material comprising a collagen matrix reinforced by a layer of a synthetic bioabsorbable material such as polylactide/polyglycolide or oxidized regenerated cellulose, and wherein oil droplets are dispersed in the collagen matrix. The oil droplets comprise 1% to 75% of the weight of the composite and result in improved leak-proofing of the composite. The composite, in the form of a sheet or a tube, is especially useful as a temporary, fully bioabsorbable prosthesis, for membranes or blood vessels where a highly leak-proof prosthesis is required. The invention also provides a method of making a composite surgical material comprising the steps of: providing a layer of a synthetic bioabsorbable material; providing a dispersion of collagen in an oil-in-water emulsion; coating at least one face of the layer of synthetic bioabsorbable material with the said dispersion; and drying the composite material thus obtained.

11 Claims, 1 Drawing Sheet

COMPOSITE SURGICAL MATERIAL

This is a Continuation-In-Part of application Ser. No. 08/437,905 filed May 10, 1995, now U.S. Pat. No. 5,660,857, which is a division of application Ser. No. 08/035,001 filed on Mar. 22, 1993, now abandoned, and a division of application Ser. No. 08/280,916 filed Jul. 27, 1994, now U.S. Pat. No. 5,789,465 which is hereby incorporated by reference.

The present invention relates to bioabsorbable composite surgical materials, processes for their preparation and also the use of such materials for the preparation of surgical prostheses and the like.

The use of bioabsorbable materials (also called resorbable materials or absorbable materials) in surgery is by now quite well known. The materials undergo gradual degradation when they are introduced into the human or animal body. This degradation results from hydrolysis which takes place on contact with living tissue in the presence of proteolytic enzymes contained therein. The hydrolysis fragments from the hydrolysis of the bioabsorbable materials are non-toxic and readily absorbed by the human or animal body.

For example, bioabsorbable surgical sutures made from copolymers of lactic and glycolic acids are in widespread use. Such sutures do not need to be removed from the wound site after wound healing is complete. Instead, the sutures undergo slow hydrolysis and absorption by the body.

Other bioabsorbable surgical materials have been used as temporary prostheses in repair surgery. For example, sheets of bioabsorbable material may be used as prostheses for regions of the pericardium or the peritoneal membrane. Healing of the damaged membrane takes place from the edges of the prosthesis, and the prosthesis is gradually absorbed as healing progresses.

Likewise, tubes of bioabsorbable surgical material have been used as arterial grafts. Once again, healing of the damaged artery is accompanied by gradual resorption of the graft.

EP-A-0194192 describes a bioabsorbable composite material that is especially suitable for use as a surgical prosthesis. The material comprises a sheet of reconstituted collagen reinforced with a mesh of a synthetic bioabsorbable polymer such as polylactic/polyglycolic acid or oxidised regenerated cellulose. The composite material is sufficiently strong to be used as an arterial graft or the like, and in particular is strong enough to hold sutures. The reconstituted collagen sheet fills all of the interstices in the mesh and renders the composite material leak-proof. The leak-proofing effect is especially important when the material is to be used to repair blood vessels. Furthermore, it has been found that the reinforced collagen films are absorbed more slowly in vivo than non-reinforced collagen films.

A defect of the reinforced collagen films described in EP-A-0194192 is that the film does not remain leak-proof in use for a sufficiently long time to be usable for some surgical applications. This is to say, the rate of bioabsorption of the collagen is sufficiently rapid that in some cases the film may start to leak through the interstices of the reinforcing mesh before wound healing is complete.

The rate of absorption of collagen in vivo can be reduced by chemical cross-linking of the collagen with succinimide or glutaraldehyde. However, such chemical treatment necessarily renders the collagen less biocompatible.

It has now been found that reinforced collagen films similar to those described in EP-A-0194192 may be made with significantly improved leak-proofing characteristics by incorporating oil droplets into the collagen layer.

The present invention provides a composite surgical material comprising a collagen matrix reinforced by a layer of a synthetic bioabsorbable material and having oil droplets dispersed in the collagen matrix.

Preferably, the oil droplets comprise from 2% to 75% by weight of the composite material, more preferably from 5% to 50% by weight of the composite material, and most preferably from 10% to 40% by weight of the composite material.

The oil droplets are preferably microdroplets such that at least 90% of the droplets have diameters in the range 0.1 $\mu$m to 250 $\mu$m. More preferably, at least 90% of the droplets have diameters in the range 1 $\mu$m to 50 $\mu$m.

The oil droplets are preferably distributed uniformly throughout the collagen matrix. However, in certain embodiments, the oil droplets may be distributed non-uniformly, for example to provide different rates of bioabsorption of the collagen matrix in different regions of the composite material.

The oil may be any bioabsorbable and biocompatible oil. For example, vegetable oils such as corn oil, sunflower seed oil, sesame seed oil or linseed oil may be used. The term "oil" also encompasses oleaginous materials, such as lanolin, that are solid or semisolid at room temperature.

The collagen matrix preferably comprises insoluble fibrous collagen, such as insoluble Type I and/or Type III collagen fibres. The collagen matrix may additionally comprise soluble collagen, such as gelatin or atelocollagen, or acid - soluble collagen, or even collagen fibres reconstituted from these soluble collagens. The collagen may be obtained from any animal, fish or avian source, but is preferably obtained from bovine corium.

The relative amounts of the collagen matrix and the synthetic bioabsorbable material in the composite surgical materials according to the present invention may vary widely, depending on the intended use of the materials and the desired rate of bioabsorption. The composite materials preferably contain from 10% to 95% by weight of the collagen matrix (including the oil droplets and any other substances dispersed therein). Preferably, the composite materials contain from 20% to 60% by weight of the collagen matrix.

The reinforcing layer is formed from a synthetic bioabsorbable material. Preferred synthetic bioabsorbable materials include synthetic suture materials such as polymers or copolymers of lactic and/or glycolic acids. Other preferred synthetic bioabsorbable materials include modified celluloses, such as oxidised regenerated cellulose. Particularly preferred synthetic bioabsorbable materials include the polylactic/polyglycolic acid copolymer sold under the Registered Trade Mark VICRYL and the oxidised regenerated cellulose sold under the Registered Trade Mark SURGICEL.

The layer of synthetic bioabsorbable material is preferably in the form of a knitted, woven or non-woven mesh or web. This arrangement combines flexibility with sufficient strength for the composite material to hold sutures. The foraminous nature of these reinforcing layers also assists suturing. The mesh size selected for the layer of synthetic bioabsorbable material can very widely, depending on the particular surgical application that is envisaged.

The composite surgical materials according to the present invention preferably further comprise pharmacologically active agents dispersed in the collagen matrix. Preferred pharmacologically active agents include antibiotics, antiseptics, anti-inflammatory agents and agents that promote wound healing, such as cytokines or glycosaminoglycans (e.g. hyaluronic acid and its salts, heparin and the like).

The pharmacologically active agents are preferably present in an amount of 0.01%–5% by weight, more preferably 0.01%–1% by weight based on the total weight of the composite material. It will be appreciated that the presence of the oil droplets allows oleophilic active agents to be dispersed in the collagen matrix as well as hydrophilic active agents.

The composite surgical materials according to the present invention are preferably in the form of a flat sheet or a tube.

The present invention also encompasses the use of the above composite surgical materials for the preparation of a bioabsorbable surgical graft or prosthesis. For example, flat sheets of the material according to the present invention may be used as membrane grafts for repair of the peritoneum or pericardium. Tubes of the material according to the present invention may be used as grafts for the repair of blood vessels. It has been found, surprisingly, that the sheets and tubes of material according to the present invention remain leak-proof for substantially longer than corresponding materials prepared in accordance with EP-A-0194192.

The present invention also provides a process to prepare a composite surgical material comprising the steps of: providing a layer of a synthetic bioabsorbable material; providing a dispersion of collagen in an oil-in-water emulsion; coating at least one face of the layer of synthetic bioabsorbable material with the said dispersion; and drying the composite material thus obtained.

Preferably, the step of providing a dispersion of collagen in an oil-in-water emulsion comprises adding the collagen and the oil to water followed by emulsifying the oil at high shear. Emulsifiers may be added to assist this process, but are not always necessary, since collagen is an effective emulsifier. Where the oil is a solid or semisolid oleaginous material at room temperature (e.g. lanolin), the emulsification step is carried out at an elevated temperature, at which the oil is liquid.

Preferably, the weight ratio of collagen to oil in the emulsion is from 10:1 to 1:10, more preferably is from 2:1 to 1:5, and most preferably it is from 1:1 to 1:3. Preferably, the concentration of collagen in the emulsion is from 0.05% w/v to 10% w/v, more preferably 0.1% w/v to 5% w/v.

Preferably, the collagen, oil and synthetic bioabsorbable polymer are as defined above for the preferred embodiments of the composite surgical material according to the present invention.

Specific embodiments of the present invention will now be described further, by way of example, with reference to the accompanying Figures, in which:

EXAMPLE 1

Figure 1:
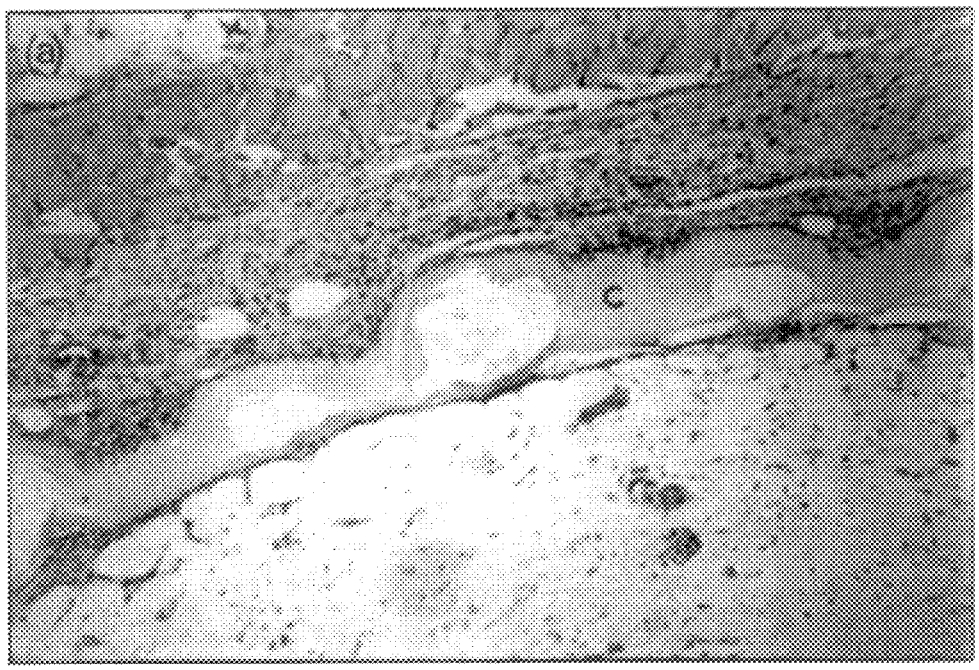
FIG. 1 shows a photomicrograph of a cross section through a collagen/vicryl film subcutaneous inplant after 14 days.

Reinforced collagen films according to the present invention are prepared as follows.

Fibrous collagen obtained from bovine corium, prewashed to remove the majority of non-collagenous components as described in U.S. Pat. No. 4,614,794 or U.S. Pat. No. 4,320,201 is suspended in clear, deionised pyrogen-free water and homogenised to a fine fibrous suspension by passage through a homogenising system, such as that described in U.S. Pat. No. 4,320,201. The collagen suspension is then acidified by addition of acetic acid at a concentration of 0.05M. The concentration of collagen fibres in the dispersion is 0.5% w/v.

To this suspension is added sesame seed oil at 50%, 100%, 200%, or 500% (as % of the collagen content, w/w). The mixture is homogenised to form an emulsion, degassed under vacuum, and poured into trays. In the trays a mesh of poly(L-lactide) poly(L-glycolide) (supplied by Ethicon Inc. under the Registered Trade Mark VICRYL, style 9) is immersed in the collagen/oil emulsion. The emulsions are dried in air at room temperature to form films.

For comparison purposes a film was made in identical fashion, but with zero oil content.

EXAMPLE 2

The permeability to physiological saline of films prepared in accordance with Example 1 is determined as follows.

Pieces of collagen/oil/Vicryl™ film (oil content with respect to collagen: 0 (comparative example), 50%, 200%, 500%) are clamped between two hollow, flanged, cylindrical chambers (2.5 cm diameter) to form a water-tight seal. This apparatus is suspended vertically over a beaker in a humidified chamber at 37° C. 25 ml of phosphate-buffered saline is placed in the upper chamber. The volume permeating through the film is collected in the beaker and measured daily, at which time the volume of saline in the upper chamber is replenished to 25 ml.

The results are expressed as the cumulated volume of saline which has passed through the films. During the first 9 days there is no significant difference in permeability between the different films. However, from days 10 to 17 there is a significant variation in permeability which correlates with the oil content of the films:

| Oil content (%) | vol.(ml)days 1–9 | vol.(ml)days 10–17 |
| --- | --- | --- |
| 0 (comparative) | 81 | 137 |
| 50 | 70 | 106 |
| 200 | 74 | 101 |
| 500 | 82 | 82 |

EXAMPLE 3

The effect of oil content on the susceptibility of reinforced collagen films to degradation by collagenase is determined as follows.

Pieces of film prepared as in Example 1 are cut to give a collagen content of approx. 50 mg. These are incubated at 37° C. in 32.5 ml of Tris buffer (pH7.2) containing bacterial collagenase (Clostridiopeptidase A) at 50 U/ml for 2.5 h. collagen degradation is measured by hydroxyproline assay of aliquots of the supernatant solution after centrifugation, and expressed as a % of the starting collagen content of the sample.

Collagen degradation was significantly decreased in films containing oil at 200% and 500% of the weight of collagen (degradation: 63.9% and 49.2%, respectively, compared with 85.0% degradation of collagen film containing no oil).

EXAMPLE 4

The effect of oil content on the susceptibility of reinforced collagen films to degradation in vivo is determined as follows.

Figure 2:
FIG. 2 shows a photomicrograph of a cross section through a collagen/oil/vicryl film subcutaneous inplant (500% oil/collagen w/w) after 14 days.

Pieces of film (0.5 cm×1 cm) prepared as in Example 1 are implanted subcutaneously in 10 wk old Wistar rats, which are sacrificed at 7 and 14 days. The implant and surrounding tissue are excised, fixed, paraffin-wax embedded, sectioned and stained with haematoxylin/eosin. All the films containing oil have retained their integrity and showed significantly less degradation than those without oil at both time-points. This is illustrated in the Figures, in which the remaining reinforced collagen film after 14 days is labelled C. The oil-free film in FIG. 1 (comparative example) clearly shows more degradation than the film according to the present invention shown in FIG. 2.

The above embodiments have been described by way of example only. Many other embodiments falling within the scope of the accompanying claims will be apparent to the skilled reader.

We claim:

1. A process to prepare a composite surgical material comprising the steps of:

providing a layer of a synthetic bioabsorbable material;

providing a dispersion of collagen in an oil-in-water emulsion;

coating at least one face of the layer of synthetic bioabsorbable material with the said dispersion; and drying the composite material thus obtained.

2. A process according to claim 1 wherein the step of providing a dispersion of collagen in an oil-in-water emulsion comprises mixing the collagen and the oil with water followed by emulsifying the oil.

3. A process according to claim 1 or 2, wherein the collagen comprises insoluble fibrous collagen.

4. A process to prepare a composite surgical material comprising the steps of:

providing a layer of synthetic bioabsorbable material;

providing a dispersion of collagen in an oil-in-water emulsion, wherein the weight ratio of collagen to oil in the said emulsion is from 2:1 to 1:5;

coating at least one face of the layer of synthetic bioabsorbable material with the said dispersion; and drying the composite material thus obtained.

5. A process according to claim 4, wherein the weight ratio of collagen to oil in the said emulsion is from 1:1 to 1:5.

6. A process according to claim 5, wherein the weight ratio of collagen to oil in the said emulsion is from 1:1 to 1:3.

7. A process according to any of claims 1 to 6, wherein the synthetic bioabsorbable material comprises a polymer or copolymer of lactic acid and/or glycolic acid.

8. A process according to any of claims 1 to 7, wherein the synthetic bioabsorbable material comprises oxidised regenerated cellulose.

9. A process according to any of claims 1 to 8, wherein the layer of synthetic bioabsorbable is a knitted, woven or non-woven mesh or web.

10. A process according to any of claims 1 to 9, further comprising the step of dispersing an antibiotic, an antiseptic or an anti-inflammatory compound in the said oil-in-water emulsion.

11. A process according to any of claims 1 to 10, further comprising the step of dispersing a growth factor, a cytokine and/or a glycosamino glycan in the said oil-in-water emulsion.

* * * * *